US00PP29303P3

(12) United States Plant Patent
Higaki

(10) Patent No.: US PP29,303 P3
(45) Date of Patent: May 22, 2018

(54) ***HYDRANGEA* PLANT NAMED 'BCHY-11.026'**

(50) Latin Name: ***Hydrangea macrophylla* (Thunb.)**
Varietal Denomination: BCHY-11.026

(71) Applicant: Harrison M. Higaki, San Mateo, CA (US)

(72) Inventor: Harrison M. Higaki, San Mateo, CA (US)

(73) Assignee: Bay City Flower Company, Half Moon Bay, CA (US)

( * ) Notice: Subject to any disclaimer, the term of this patent is extended or adjusted under 35 U.S.C. 154(b) by 11 days.

(21) Appl. No.: 14/999,797

(22) Filed: Jun. 27, 2016

(65) Prior Publication Data

US 2017/0374778 P1 Dec. 28, 2017

(51) Int. Cl.
*A01H 5/00* (2006.01)
*A01H 5/02* (2018.01)

(52) U.S. Cl.
USPC ..... Plt./250
CPC ..... *A01H 5/02* (2013.01)

(58) Field of Classification Search
USPC ..... Plt./250
See application file for complete search history.

(56) References Cited

PUBLICATIONS https://vnps.org/princewilliamwildflowersociety/download/wild_news/2015_-_wild_news_archive/WILD%20NEWS%20May-June%202015%20final.pdf (retireved from Internet on Sep. 6, 2017).*

* cited by examiner

*Primary Examiner* — Susan McCormick Ewoldt
(74) *Attorney, Agent, or Firm* — James R. Cypher; Charles R. Cypher

(57) ABSTRACT

A new and distinct cultivar of *Hydrangea macrophylla* (Thunb.) named 'BCHY-11.026' originated as a controlled cross between varieties. The variety 'BCHY-11.026' has attractive inflorescences with relatively large sepalous florets, attractive, nonuniform sepal pigmentation and good commercial characteristics. Sepalous florets surround the non-sepalous florets in the center of the inforescence.

2 Drawing Sheets

Botanical classification: *Hydrangea macrophylla* (Thunb.) 'BCHY-11.026'.

Variety denomination: 'BCHY-11.026'.

BACKGROUND OF THE INVENTION

This invention relates to a new and distinct cultivar of the Hydrangeaceae family. The botanical name of the plant is *Hydrangea macrophylla* (Thunb.) 'BCHY-11.026'.

The new cultivar originated as a seedling from a controlled cross between the unpatented variety known as '8.1' which was the seed parent and the variety 'BC8.3' which was the pollen parent. The pollen parent, 'BC8.3', is the subject of U.S. Plant Pat. No. 25,507, filed Apr. 8, 2013, and issued May 5, 2015. The parent '8.1' has attractive inflorescences but a growth habit that is not suitable for commercial production of ornamental potted plants. The plant 'BC8.3' has compact, attractive inflorescences with relatively large sepalous florets that surround and almost hide all of the non-sepalous florets in the center of the panicle, attractive sepal pigmentation, and stems that branch easily and are relatively strong.

The new variety 'BCHY-11.026' has relatively large sepalous florets, non-uniform sepal pigmentation at maturity and good commercial characteristics. 'BCHY-11.026' has compact, attractive inflorescences with relatively large sepalous florets that surround the non-sepalous florets in the center of the panicle. The color of the sepals changes as the plant ages. Below is a table comparing the new variety to similar varieties, including the variety 'BCHY-11.033' which is the subject of U.S. Plant Pat. No. 26,407 and resulted from the same cross. The present variety 'BCHY-11.026' differs from patented variety 'BCHY-11.033' in that non-sepalous florets of the inflorescence of 'BCHY-11.033' are almost hidden by the sepalous florets, while the non-sepalous florets of the present variety 'BCHY-11.026' are not hidden by the surrounding sepalous florets. Also the inflorescence of the present variety 'BCHY-11.026' is smaller than the inflorescence of 'BCHY-11.033'. The inflorescence of 'BCHY-11.026' is 7" in diameter and 3" high, while the inflorescence of 'BCHY-11.033' is 9" in diameter and 4" high.

TABLE 1

| | New Variety 'BCHY-11.026' | U.S. Plant Pat. No. 23,757 'BC6.1' | U.S. Plant Pat. No. 25,507 'BC8.3' | Commercial variety 'Venedig' which may be U.S. Plant Pat. No. 10,928 'Venice Raven' | U.S. Plant Pat. No. 26,407 'BCHY-11.033' |
|---|---|---|---|---|---|
| Leaf size | 8 cm wide × 10 cm long | 12 cm wide × 15 cm long | 10 cm × 16 cm | 11 cm wide × 15.5 cm long - source U.S. Plant Pat. No. 10,928 | 9.5 cm wide × 12.5 cm long |

TABLE 1-continued

| | New Variety 'BCHY-11.026' | U.S. Plant Pat. No. 23,757 'BC6.1' | U.S. Plant Pat. No. 25,507 'BC8.3' | Commercial variety 'Venedig' which may be U.S. Plant Pat. No. 10,928 'Venice Raven' | U.S. Plant Pat. No. 26,407 'BCHY-11.033' |
|---|---|---|---|---|---|
| Plant height | 13" in 4.5" pot. | 15" in 6" pot. | 15" in 6" pot | 12" in 6" pot - observed controls grown alongside 'BC6.1'. | 13" in 6" pot |
| Stem strength | Strong | Stems are strong but benefit from being staked | Stems are relatively strong. | Strong - observed controls grown alongside 'BC6.1'. | Strong |
| Sepal Pigmentation | Both sides of sepals are R.H.S. 68 C. (red - purple group). | Upper side of sepals is R.H.S. 86 A (violet group); Under side of sepals is R.H.S. 88 D (violet group) | Upper side of sepals is R.H.S. 73A (red - purple group) in center, and margins of sepals are R.H.S. 56 A (red group). | Upper side of sepals is R.H.S. 84 A (violet group). Under side of sepals is R.H.S. 85 A (violet group) observed controls grown alongside 'BC6.1'. | Both sides of sepals are R.H.S. 68 C. (red - purple group) |
| Sepalous Floret Size - Diameter | 70 mm | 70 mm | 50 mm to 60 mm | 70 mm - observed controls grown alongside 'BC6.1'. | 70 mm |

The new cultivar 'BCHY-11.026' has been successfully asexually reproduced under controlled environmental conditions at a nursery in Half Moon Bay, Calif. under the direction of the inventor with its distinguishing characteristics remaining stable.

Asexual reproduction was first accomplished when vegetative cuttings were taken from the initially selected plant. Examination of asexually reproduced, successive generations grown in Half Moon Bay, Calif. show that the combination of characteristics as herein disclosed for 'BCHY-11.026' remains firmly fixed.

DESCRIPTION OF THE DRAWINGS

The accompanying drawings consist of color photographs that show the typical plant form, including the inflorescence, foliage, and sepals.

DESCRIPTION OF THE NEW PLANT

Figure 1:
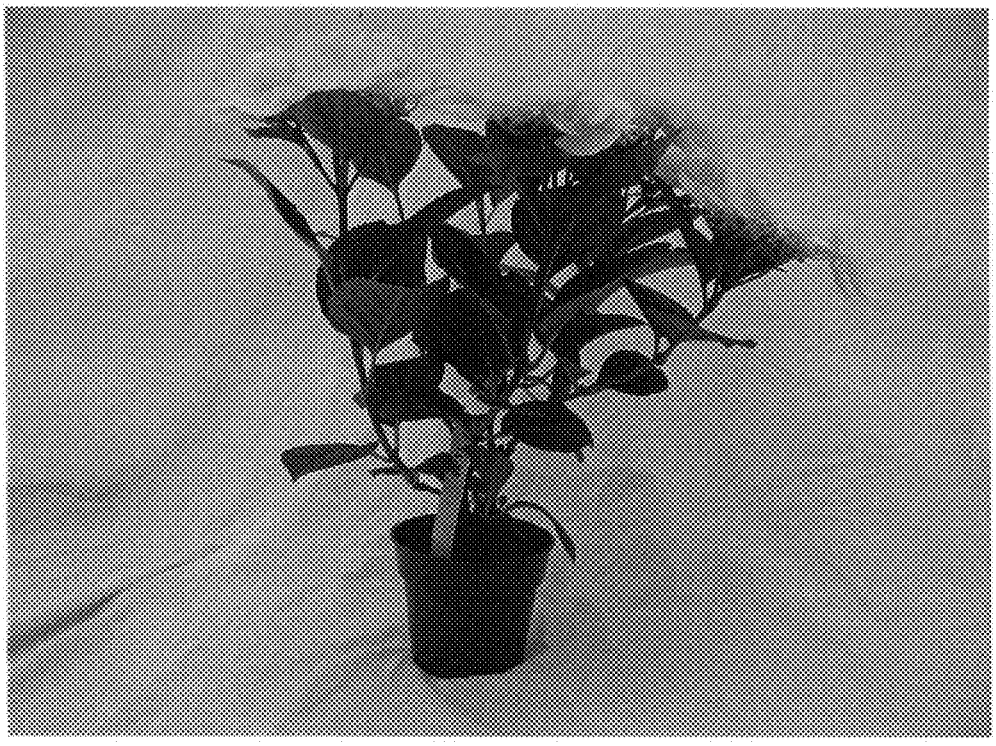
FIG. 1 is a view of the entire plant showing its form, growth habit, dark green foliage, inflorescence, and the color of its sepals.
Figure 2:
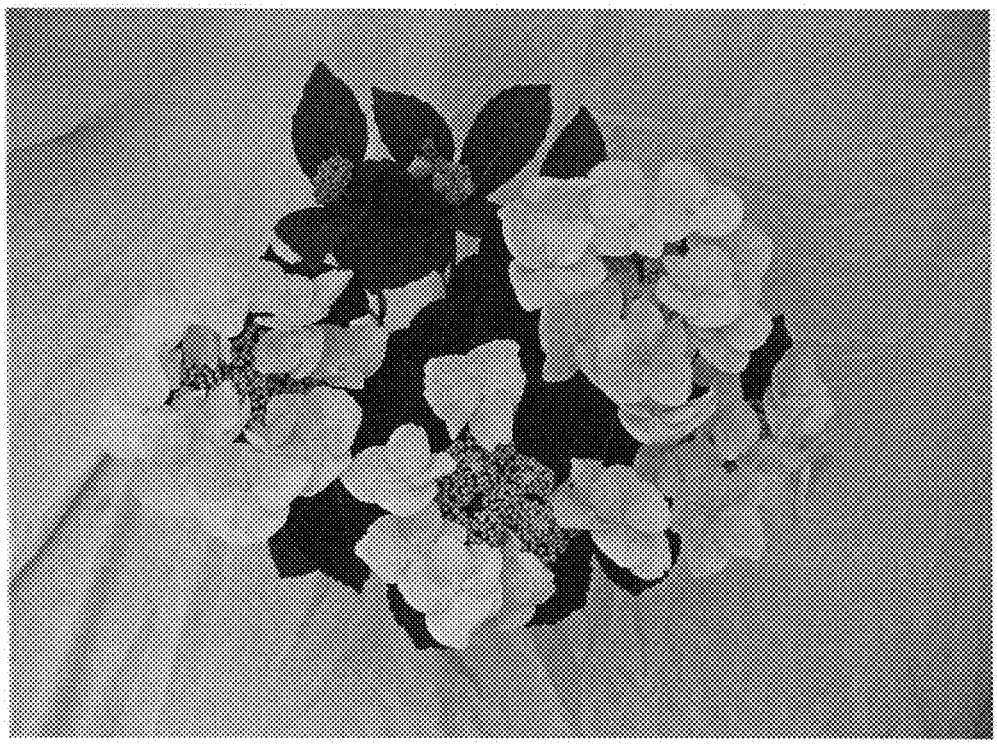
FIG. 2 is a top view of the entire plant showing its form, growth habit, dark green foliage, inflorescence, and the color of its sepals.
Figure 3:
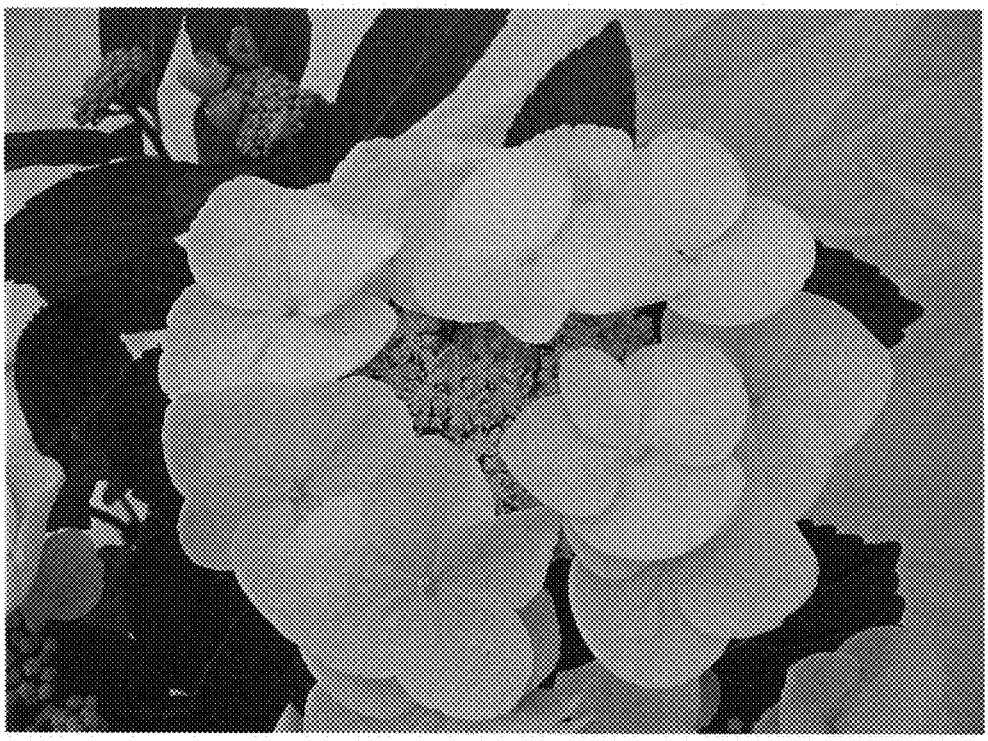
FIG. 3 is a top view of an inflorescence.
Figure 4:
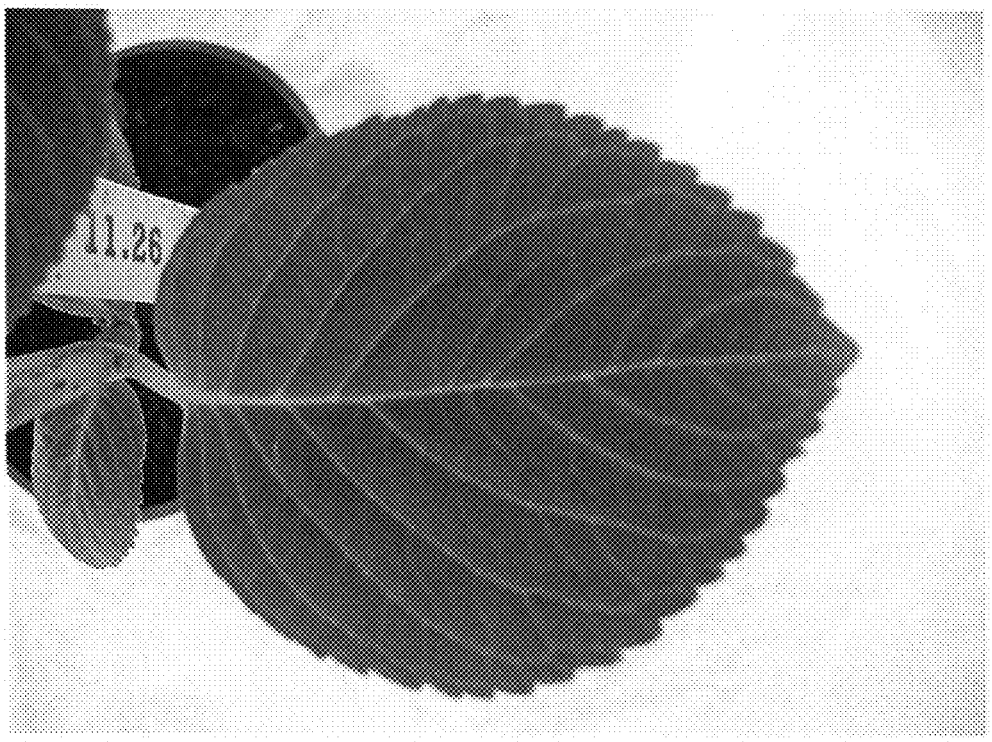
FIG. 4 is a close-up view of the adaxial surface of a mature leaf.

The plant shown is approximately a year old. The plant started out as cuttings, taken from the stem of a grown plant. The plant was pinched early to promote lateral branches.

'BCHY-11.026' has not been observed under all possible environmental conditions. The phenotype may vary significantly with variations in environment such as temperature, light intensity, treatment with aluminum and day length. Color determinations were made with The Royal Horticultural Society (R.H.S.) Colour Chart, developed in association with the Flower Council of Holland, located in Lieden. The plant:

*Origin*.—Controlled cross. The new cultivar originated as a seedling from a controlled cross between the unpatented variety known as '8.1' which was the seed parent and the commercial variety 'BC8.3' which was the pollen parent. 'BC8.3' is the subject of U.S. Plant Pat. No. 25,507.

*Form*.—Upright, non-climbing, compact shrub. A typical plant that is approximately a year old with a mature inflorescence that is ready for sale is approximately 13" high and has a diameter of 16" when grown in a 4.5" pot with appropriate soil amendments.

*Growth*.—Upright, vigorous growth habit. Inflorescence is medium. The plant branches easily with shoots forming at the base of the plant. Lateral branches are similar in appearance and form to the main stems.

*Stems*.—Stems are 10" long. Fasciation is absent. Lenticels are present. Lenticels are R.H.S. 86 A (violet group) and are 1 to 3 mm long. The surface of young stems is glabrous. Stems become woody as they age. The color of typical young stems and young lateral branches is R.H.S. 145 A (yellow-green group). The older portions of the stems are R.H.S. 199 A (grey-brown group). Younger portions of the stems are 5 mm in diameter. Older portions of the stems are 5-7 mm in diameter.

*Foliage*.—Abundant. Leaves are opposite on stem and lateral branches. Shape of leaf. — Ovate with rounded base and acute apex. Leaf blade margins are serrate and not lobed. Texture. — Glabrous; veins dominate on the underside of the leaf and are sunken on the upper leaf surface. Color. — Mature leaves have an upper side that is R.H.S. 137 A (green group), and an under side that is R.H.S. 138 A (green group). Leaves are moderately glossy. Variegation is absent. Leaves are pinnately veined. The midvein and veins branching off the midvein are large and prominent on the underside of the leaves. Veins are R.H.S. 145 A (yellow-green group). Leaves are as wide as 8 cm and 10 cm long. Petioles are smooth and approximately 3 cm long and 4 mm wide. Petioles are R.H.S. 145 A (yellow-green group).

Buds:

*Form*.—Globose with 4 to 5 connate, elliptic, smooth petals. Most buds, whether they will mature into sepalous or non-sepalous florets, have 5 petals. Buds in the center of the inflorescence are non-sepalous. The minority of buds will develop into sepalous florets. The buds are approximately 2 mm by 2 mm when very young. Buds can be 5 mm in diameter and still unopened. Color of mature buds is R.H.S. 73 C (red-purple group).

*Aspect*.—Smooth.

*Arrangement*.—Borne on branched panicles.

Inflorescence:

*Form*.—Paniculate. Terminal. As many as 150 individual florets (both sepalous and non-sepalous) per inflorescence. Both sepalous florets and non-sepalous florets borne on the same panicle. Flowers do not produce a fragrance. The peduncle for the inflorescence is strong and upright. Many non-sepalous florets developing early on cymes that are later surrounded by the sepalous florets that form at the outside of the panicle. Non-sepalous florets are conspicuous. Florets, both sepalous and non-sepalous, have anthers and style. Inflorescences are long-lasting, up to six weeks.

*Size of inflorescence*.—Compact and flat. Individual inflorescence size is dependent on the number of florets. A typical inflorescence can grow as large as 7" in diameter, and 3" high.

*Shape*.—Clusters of numerous small florets; sepalous florets overlap one another. Sepals are persistent.

*Appearance*.—Not showy.

Florets:

*General*.—The non-sepalous florets at the center of the inflorescence open first. Sepalous and non-sepalous florets are perfect and complete. Corolla: Generally, for both sepalous and non-sepalous florets there are 5 petals. Petals fall off easily of the non-sepalous florets. Petals are typically 4 mm long and 3 mm wide. Petals are R.H.S. 155 D (white group). Few lenticels are present on pedicels of both sepalous and non-sepalous florets, lenticels are no more than 1 mm long and very narrow. Lenticels are R.H.S. 59 B (red-purple group). Pedicel length for non-sepalous florets averages 4 mm. Pedicel length of sepalous florets is approximately 20 to 25 mm in length for plants of this age. Pedicels of both sepalous and non-sepalous florets continue to elongate as the inflorescence ages. Pedicels can be 73 D (red-purple group) to R.H.S. 145 C (yellow-green group) near floret when mature.

*Stamens*.—8 to 10 stamens. Filament is approximately 2 to 4 mm long. Filament is R.H.S. 73 D (purple group). Anther is 1 mm long, regular and basally attached. Pollen is scarce.

*Stigma*.—Two to three style each, although most florets have two style. Each style has one stigma. Style is typically 1 mm long. Style is R.H.S. 73 D (red-purple group). Stigma is R.H.S. 73 D (purple group).

*Ovary*.—Ovary is partially inferior.

*Sepalous florets*.—General. — Veins dominate on the underside of the sepals. Number of sepals. — 4 to 5 sepals per floret, usually 4. Aspect of sepals. — Smooth and glaucescent. Shape of sepals. — Reniform with acuminate apex. Edges are entire, but with much crenation. Size of sepals. — Sepals at maturity are typically 40 mm long and 40 mm wide. Sepalous florets are typically 70 mm in diameter. The upper sides of the sepals are R.H.S. 68 C (red-purple group) and the undersides are the same. Pigmentation develops at the tips of the sepals and travels inward towards base of the sepals. Pigmentation lightens as the sepals reach maturity. Pigmentation of mature florets is 73 D (red-purple group).

*Fruit*.—None.

*Disease and pest resistance*.—Unknown.

Plants prefer milder temperatures.

Plants bloom in the spring but can be forced to bloom by placing in a cold environment.

I claim:

1. A new and distinct *Hydrangea macrophylla* plant named 'BCHY-11.026' substantially as herein illustrated and described.

* * * * *